(12) United States Patent
Dutta et al.

(10) Patent No.: US 12,241,841 B2
(45) Date of Patent: Mar. 4, 2025

(54) SYSTEM AND METHOD FOR NON-INVASIVE REAL-TIME PREDICTION OF LIQUID FOOD QUALITY WITHIN ENCLOSED PACKAGE

(71) Applicant: Tata Consultancy Services Limited, Mumbai (IN)

(72) Inventors: Jayita Dutta, Pune (IN); Parijat Deshpande, Pune (IN); Beena Rai, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 807 days.

(21) Appl. No.: 17/504,823

(22) Filed: Oct. 19, 2021

(65) Prior Publication Data

US 2022/0120693 A1   Apr. 21, 2022

(30) Foreign Application Priority Data

Oct. 20, 2020   (IN) .............................. 202021045758

(51) Int. Cl.
  *G01N 21/78*   (2006.01)
  *G01N 33/02*   (2006.01)
  *G06Q 10/087*   (2023.01)

(52) U.S. Cl.
  CPC ............. *G01N 21/78* (2013.01); *G01N 33/02* (2013.01); *G06Q 10/087* (2013.01)

(58) Field of Classification Search
  CPC ................... G01N 21/78; G01N 33/02; G01N 2021/7759; G06Q 10/087
  See application file for complete search history.

(56) References Cited

FOREIGN PATENT DOCUMENTS

KR   200376182 Y1   3/2005

OTHER PUBLICATIONS

Kuswandi et al., "Smart packaging: sensors for monitoring of food quality and safety," Sens. & Instrumen. Food Qual., 5:137-146 (2011).
Listyarini et al., "A paper-based Colorimetric Indicator Label using Natural Dye for Monitoring Shrimp Spoilage," IOP Conf. Series: Materials Science and Engineering, 367 (2018).
Liu et al., "Application of Gold-Nanoparticle Colorimetric Sensing to Rapid Food Safety Screening," Sensors 18:4166 (2018).

(Continued)

*Primary Examiner* — A. Hunter Wilder
(74) *Attorney, Agent, or Firm* — FINNEGAN, HENDERSON, FARABOW, GARRETT & DUNNER LLP

(57) ABSTRACT

State of the art food quality measurement techniques fail to determine quality of the food item once it is packed and sealed in a container. The disclosure herein generally relates to food quality prediction, and, more particularly, to a system and method for predicting food quality in a non-invasive manner. A Color Changing Indicator (CCI) in a biosensor strip forming a component of the enclosed package in which the liquid food item is packed, changes color when came in contact with the liquid food item. For different quality of the liquid food item the CCI has different color. Based on the color of the CCI, and ambient temperature and relative humidity at the time the color of the CCI is determined, a machine learning model determines rate of deterioration of the liquid food item, and then predicts remaining shelf life, which in turn provided as output to a user.

3 Claims, 9 Drawing Sheets

(56) References Cited

OTHER PUBLICATIONS

Mohebi et al., "Intelligent packaging in meat industry: An overview of existing solutions," J Food Sci Technol 52(7): 3947-3964 (2015).
Sarkar et al., "Nanosensors in food safety," Chapter 10 (2017).
Tichoniuk et al., "The Application of Natural Dyes in Food Freshness Indicators Designed for Intelligent Packaing," Studia Oeconomica Posnaniensia, 5:7 (2017).

SYSTEM AND METHOD FOR NON-INVASIVE REAL-TIME PREDICTION OF LIQUID FOOD QUALITY WITHIN ENCLOSED PACKAGE

PRIORITY CLAIM

This U.S. patent application claims priority under 35 U.S.C. § 119 to: Indian provisional Application No. 202021045758, filed on Oct. 20, 2020. The entire contents of the aforementioned application are incorporated herein by reference.

TECHNICAL FIELD

This disclosure relates generally to food quality prediction, and more particularly to a system and method for predicting food quality in a non-invasive manner.

BACKGROUND

In order to enhance shelf-life, liquid food-items are packaged within air-tight enclosed package. Such enclosed packages may include various layers to prevent the exposure of the liquid food item with outside environment, thus imparting a comparatively longer shelf-life to the packaged liquid food than those liquid food items that are kept with improper packaging or no packaging. However, even with use of such packaging, there are scenarios that leads to huge wastage of packaged food items.

The inventors here have recognized several technical problems with such conventional systems, as explained below. The liquid food-items within the air-tight containers cannot be evaluated for their quality post packaging i.e., once the air-tight containers are sealed, the information about the quality of the contents within the air-tight containers is not available and one has to rely solely on the printed date on the packaging of the air-tight containers. Further, at times this can prove to be misleading and contents of the air-tight containers may be good post expiry or worse and inedible even prior to expiry. Such situations can arise due to temperature shocks received by the air-tight containers during its shelf and transportation life-time.

Main reason behind said food wastage is inability to monitor the variation of food quality in real-time under different supply chain scenarios. To address this challenge real time monitoring and prediction of food quality for variety of foods becomes essential. This would enable dynamic decisions on rerouting, repurposing, and recycling.

SUMMARY

Embodiments of the present disclosure present technological improvements as solutions to one or more of the above-mentioned technical problems recognized by the inventors in conventional systems. For example, in one embodiment, a method for non-invasive real-time prediction of quality of a liquid food item within enclosed package is provided. The method includes the following steps. Initially, color of a Color Changing Indicator (CCI) in a bio-sensor strip forming a component of the enclosed package is determined, when the liquid food item comes in contact with the CCI, via one or more hardware processors. The CCI includes a transparent poly-di-methyl-siloxane (PDMS) substrate, a thin film layer of bio-edible and bio-compatible color changing pigments, wherein the bio-edible and bio-compatible color changing pigments change color by interacting with one or more chemical components of the liquid food item, wherein a plurality of physio-thermal properties of each of the one or more chemical components vary with degradation of the liquid food item, and an optical device, wherein the color change of the color changing pigments is visible through a transparent lens of the optical device. Further, the information on a) the determined color of the CCI, and b) a measured ambient temperature and relative humidity inside the enclosed package while determining the color of the CCI inside the enclosed package, are processed using a machine learning data model, wherein the machine learning data model determines value of a remaining shelf life of the liquid food item. Further, a result indicating the determined value of the remaining shelf life of the liquid food item is generated.

In another aspect, a system for non-invasive real-time prediction of quality of a liquid food item within enclosed package is provided. The system includes one or more hardware processors, a communication interface (206), and a memory storing a plurality of instructions, wherein the plurality of instructions when executed, cause the one or more hardware processors to initially determine color of a Color Changing Indicator (CCI) in a bio-sensor strip forming a component of the enclosed package, when the liquid food item comes in contact with the CCI. The CCI includes a transparent poly-di-methyl-siloxane (PDMS) substrate, a thin film of bio-edible and bio-compatible color changing pigments, wherein the bio-edible and bio-compatible color changing pigments change color by interacting with one or more chemical components of the liquid food item, wherein a plurality of physio-thermal properties of each of the one or more chemical components vary with degradation of the liquid food item, and an optical device, wherein the color change of the color changing pigments is visible through a transparent lens of the optical device. The system then processes information on a) the determined color of the CCI, b) a measured ambient temperature inside the enclosed package while determining the color of the CCI, and c) a measured relative humidity inside the enclosed package while determining the color of the CCI, using a machine learning data model, wherein the machine learning data model predicts the remaining shelf life of beverages. Further, the system generates a result indicating the determined value of the remaining shelf life of the liquid food item.

In yet another aspect, a non-transitory computer readable medium for non-invasive real-time prediction of quality of a liquid food item within enclosed package is provided. The non-transitory computer readable medium includes a plurality of instructions, which when executed, causes the following steps for the non-invasive real-time prediction of quality of a liquid food item within enclosed package. Initially, color of a Color Changing Indicator (CCI) in a bio-sensor strip forming a component of the enclosed package is determined, when the liquid food item comes in contact with the CCI, via one or more hardware processors. The CCI includes a transparent poly-di-methyl-siloxane (PDMS) substrate, a thin film layer of bio-edible and bio-compatible color changing pigments, wherein the bio-edible and bio-compatible color changing pigments change color by interacting with one or more chemical components of the liquid food item, wherein a plurality of physio-thermal properties of each of the one or more chemical components vary with degradation of the liquid food item, and an optical device, wherein the color change of the color changing pigments is visible through a transparent lens of the optical device. Further, the information on a) the determined color of the CCI, and b) a measured ambient temperature and relative humidity inside the enclosed package while determining the color of the CCI inside the enclosed package, are processed using a machine learning data model, wherein the machine learning data model determines value of a remaining shelf life of the liquid food item. Further, a result indicating the determined value of the remaining shelf life of the liquid food item is generated.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Food wastage due to lack of any effective real-time food monitoring method has led to a huge economic loss. This situation can be avoided if there is a provision for monitoring the food quality in real-time which can appraise the consumers regarding the food quality inside the package in real-time. Accordingly, even if the expiry date for food item is reached, and the food inside package is still consumable and in good quality, then the stake holders such as retailers, distributors and so on can opt for dynamic pricing to sell the packaged food. Customer can also rely on the quality of the food item and buy it even after the indicated expiry dates on the food package.

Hence, it is challenging to implement this conventional method for real-life supply chain scenarios.

Various embodiments disclosed herein provides method and apparatus for quality monitoring of packaged food item in a non-invasive manner. For example, in an embodiment, the disclosed apparatus includes a transparent window configured on a portion of the package for inserting a color changing indicator (CCI) or a biodetector which when come in contact with the food item may change color thereof. The change in the color may be visible from outside and may facilitate in food quality monitoring in real-time and non-invasively.

In an embodiment, the disclosed CCI may be designed and manufactured corresponding to food specific items. In an embodiment, the CCI may act as a biomarker that may undergo change in color upon coming in contact with the metabolites (gases, volatile amines etc.) released from the liquid food item contained in the package. The disclosed method results in a cost-effective real-time monitoring of food quality inside enclosed package (alternately may be referred to as "storage container" or "containers" or "package" or "package container") non-invasively by using bio-detectors. The biodetectors are further described in detail with reference to the description below.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Figure 1:
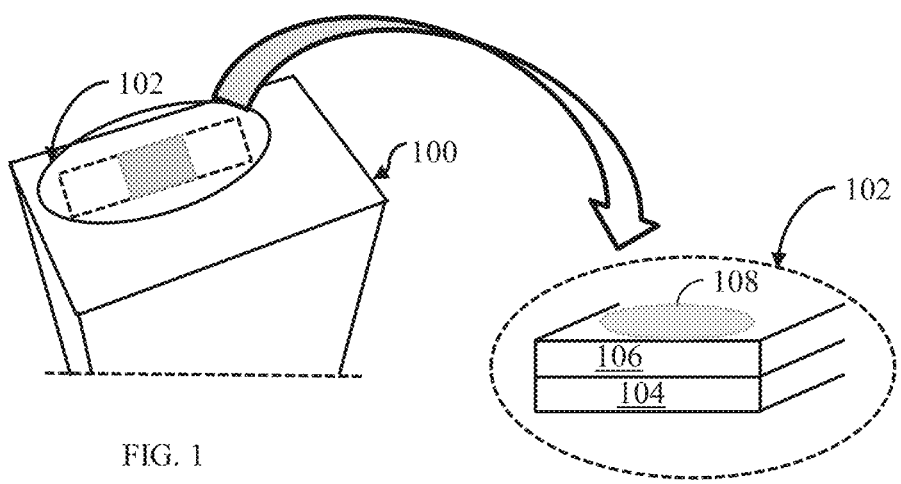
FIG. 1 illustrates an example of a liquid food container in accordance with an example embodiment of the present disclosure.

FIG. 1 illustrates an example of a food container 100 in accordance with an example embodiment of the present disclosure. For the brevity of description, the container 100 is shown to assume a cuboid shape, however it will be understood that the container 100 may assume any shape other than the shape and size shown.

In an embodiment, a biosensor 102 may be configured towards the inner walls of the container. The biosensor 102 is a color changing indicator, meaning thereby that a color change in the biosensor 102 upon coming in contact with the contents of the package or the food item may indicate a change in quality of the food-item.

In an embodiment, the biosensor 102 may be configured in form of a strip that may be configured (or attached towards the inside of the package container 100) for detecting quality of the food items therein. Herein, it will be understood that for the brevity of description and ease of understanding, the bio-sensor is shown to assume form of a rectangular shaped strip. However, in alternate implementations, the bio-sensor may assume any shape other than the shape shown here.

In an embodiment, the biosensor 102 may be made on a transparent poly-di-methyl-siloxane (PDMS) substrate 104 followed by a thin film layer 106 of bio-edible and bio-compatible color changing pigments, which is further followed by an optical device 108, for example a lens. Example of such bio-edible and bio-compatible color changing pigments may include but are not limited to, roots, flowers, leaves of plants, and other parts of plant materials that may contain a natural pigment, such as anthocyanins. It will be understood that the bio indicator (or the biosensor) is not colorless, instead the bio indicator is configured to change color upon coming in contact with the food item depending upon the quality of food item. The optical device or the lens 108 may be configured on top of the thin film layer 106 such that the color change happening in the nanoparticle layer 106 of the bio indicator 102 due to the degradation of the quality of food item inside the food container is captured by the mobile camera by illuminating mobile flash.

In an embodiment, the disclosed biosensor may be configured on any of the inside walls of the container. Additionally or alternatively, the container 100 may include a cut-out/window for configuring the biosensor 102 therein. For example, a portion of the biosensor may be outside the container through the cut-out for facilitating detection of change of color of the bio-sensor from outside the container. In an embodiment, when the biosensor is configured on the topmost wall of the container, container may be turned upside down to establish a contact between the biosensor and the food item. Upon coming in contact with the food item, the biosensor may change color thereof, which may be observed through the transparent lens via an external electronic device (as will be explained later in the description).

In an embodiment, where the biosensor is configured within the top wall of the container, the contact of the food item and the biosensor is established when the container 100 is turned upside-down, and the color of the biosensor is changed corresponding to the quality of the food item inside container. Once again, if the container is turned back and the container assumes an original resting state, the connection between the container and food item is disabled. Thus, the change in the color of the biosensor maybe observed based on the color change by the biosensor by turning the container upside down.

Herein, upon coming in contact with the food item, the biosensor may change color thereof due to the changes in physio-chemical properties (also referred to as) of various chemical components of the food item contained in the container over a period of time. The physio-chemical properties may refer to a change in, for instance, in metabolites such as volatile compounds including, but not limited to, trimethylamine (TMA), dimethylamine (DMA), and ammonia (collectively known as TVB-N), biogenic amines such as histamine, putrescine, tyramine, and cadaverine; ethanol; sulfuric compounds; and organic acids. Herein, it will be noted that the bio-marker are specific for every food item.

In an embodiment, the change in the color of the biosensor due to the changes in the physio-chemical properties of food item over a period of time may be captured by an electronic device that may be capable of predicting the quality of the food item and a remaining shelf-life of the food item. In an embodiment, the color of the food item may change progressively based on the change in the quality of the food item. In another embodiment, as the step of determining quality of the food item may be a real-time process (i.e. as and when the food item comes in contact with the biosensor), the term 'prediction' may refer to the food quality detection being done at current/present instance of time as well, and may not necessarily indicate a future quality prediction. And in the same context, prediction of the remaining shelf life serves future quality prediction of the food item. A system (embodied in the electronic device) for estimating the quality of food item contained in the packaged container, and a method therefor are explained further with reference to FIGS. 2 and 3, respectively.

Figure 2:
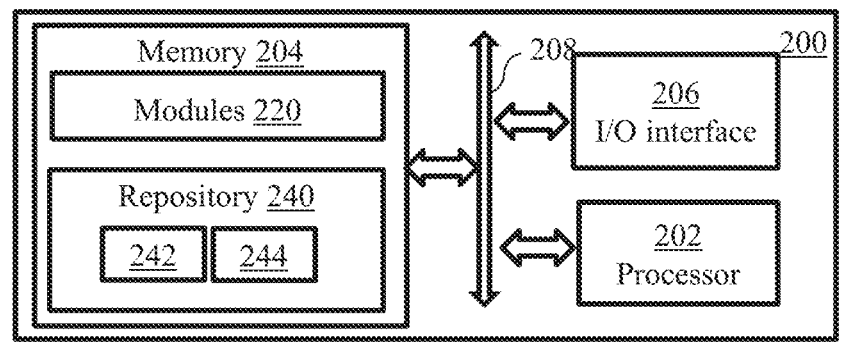
FIG. 2 illustrates a block diagram of a system for predicting quality of a liquid food item contained in a liquid food container (of FIG. 1) is illustrated, according to some embodiments of the present disclosure.

Referring now to FIG. 2, a block diagram of a system 200 for estimating quality of a food item contained in a packaged container (for example, the container 100 of FIG. 1) is illustrated, according to some embodiments of the present disclosure. The system 200 is capable of training a machine learning data model (may also be referred to as "model" or "data model" or "Artificial Intelligence (AI) model") for estimating the quality of food item based on the color of the biosensor, for example the biosensor 102 (FIG. 1). In an embodiment, the biosensor 102 may be illuminated by a light (for instance light emitted by an electronic device). The light emitted by the electronic device facilitates in avoiding confusion in understanding the color change due to other surrounding lights. Herein, it will be understood that any concentrated light source of high intensity may be utilized for illuminating the bio-sensor 102.

In an embodiment, the system 200 may predict the quality of the food item based on the color of the biosensor. Additionally, the disclosed system 200 may detect ambient temperature and a relative humidity of the food item and utilize the same for predicting the quality of the food item. In an embodiment, a micro temperature sensor and a humidity sensor may be fabricated in the biosensor 102 to configure a smart sensor. Said smart sensor (comprising the micro temperature sensor and a humidity sensor) of the biosensor may not come in contact with the food item contained inside the container. The smart sensor may be internet of things (IoT)-enabled sensors and may sense temperature and the relative humidity inside the container. The values of ambient temperature and the relative humidity sensed by the sensor may be sent to a server, for example a cloud server and the same may be picked-up by a software application (that may be installed in the electronic device or client device). In an embodiment, the system 200 may be provide the data including the color of the biosensor, and the ambient temperature and the relative humidity of the food item to the artificial intelligence (AI) model and train the same to predict the quality of food item based on the same. In an embodiment, the AI model may act as a server or may be configured in a server communicatively coupled with the system 200. During inference phase, the AI model associated with the system 200 may predict the quality collectively based on the determination of changed color, the ambient temperature and the relative humidity.

The system 200 includes or is otherwise in communication with one or more hardware processors such as a processor 202, at least one memory such as a memory 204, and an I/O interface 206. The processor 202, memory 204, and the I/O interface 206 may be coupled by a system bus such as a system bus 108 or a similar mechanism. The 1/O interface 206 may include a variety of software and hardware interfaces, for example, a web interface, a graphical user interface, and the like. The interfaces 106 may include a variety of software and hardware interfaces, for example, interfaces for peripheral device(s), such as a keyboard, a mouse, an external memory, a camera device, and a printer. Further, the interfaces 106 may enable the system 200 to communicate with other devices, such as web servers and external databases. The interfaces 106 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 106 may include one or more ports for connecting a number of computing systems with one another or to another server computer. The I/O interface 206 may include one or more ports for connecting a number of devices to one another or to another server.

The hardware processor 202 may be implemented as one or more microprocessors, microcomputers, microcontrollers, digital signal processors, central processing units, state machines, logic circuitries, and/or any devices that manipulate signals based on operational instructions. Among other capabilities, the hardware processor 202 is configured to fetch and execute computer-readable instructions stored in the memory 204.

The memory 204 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 204 includes a plurality of modules 220 and a repository 240 for storing data processed, received, and generated by one or more of the modules 220. The modules 220 may include routines, programs, objects, components, data structures, and so on, which perform particular tasks or implement particular abstract data types.

The repository 240, amongst other things, includes a system database 242 and other data 244. The other data 244 may include data generated as a result of the execution of one or more modules in the other modules 230. In an embodiment, the repository 240 may store the training data associated with the prediction of food quality. For example, the training data may include a data associated with the correlation between the color of the biosensor, and environmental conditions such as the ambient temperature, the relative humidity and so on. The training data may also include information on quality of the liquid food item corresponding to a plurality of combinations of a) the color of CCI, b) the value of the measured ambient temperature and the relative humidity.

Figure 3:
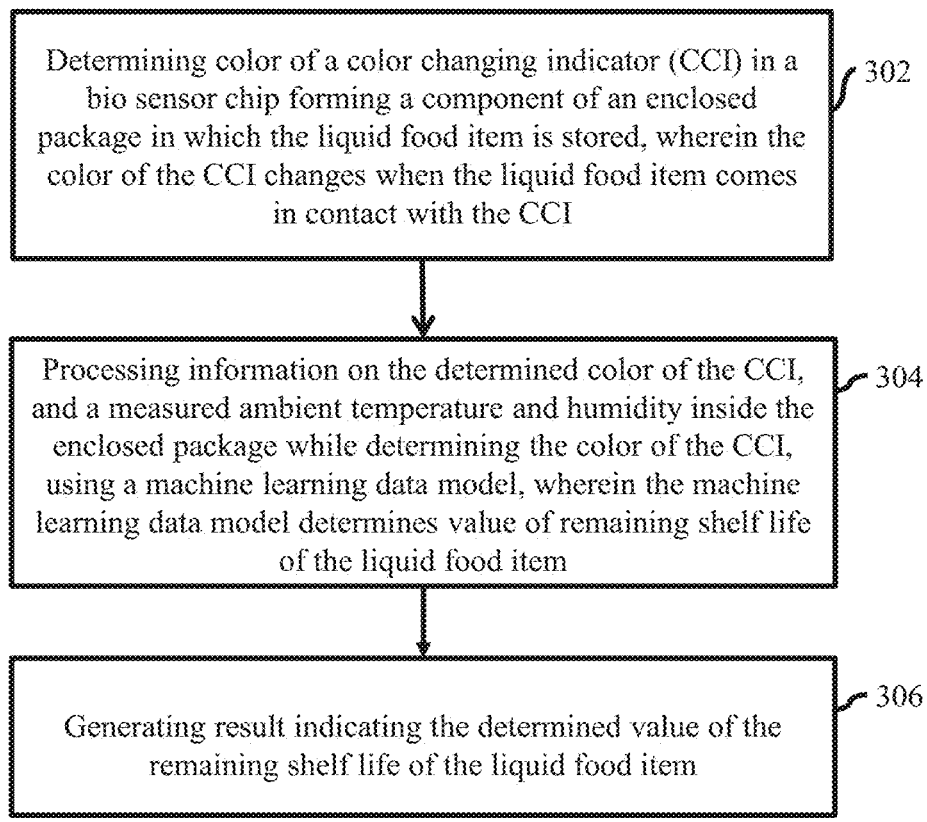
FIG. 3 illustrates a method for predicting quality of a liquid food item contained in a liquid food container, using the system of FIG. 2, in accordance with some embodiments of the present disclosure.

A method of quality estimation of a food item contained in the packaged container (for example, the container 100) by using the system (for example, the system 200) is described further with reference to FIG. 3.

Referring to FIG. 3, a flow diagram of a method 300 for quality estimation of a food item contained in the packaged container is described in accordance with an example embodiment. The method 300 depicted in the flow chart may be executed by a system, for example, the system, 200 of FIG. 2. In an example embodiment, the system 200 may be embodied in a computing device, as will be described further in the description.

Operations of the flowchart, and combinations of operation in the flowchart, may be implemented by various means, such as hardware, firmware, processor, circuitry and/or other device associated with execution of software including one or more computer program instructions. For example, one or more of the procedures described in various embodiments may be embodied by computer program instructions. In an example embodiment, the computer program instructions, which embody the procedures, described in various embodiments may be stored by at least one memory device of a system and executed by at least one processor in the system. Any such computer program instructions may be loaded onto a computer or other programmable system (for example, hardware) to produce a machine, such that the resulting computer or other programmable system embody means for implementing the operations specified in the flowchart. It will be noted herein that the operations of the method 300 are described with help of system 200. However, the operations of the method 300 can be described and/or practiced by using any other system.

At 302, the method 300 includes determining the color of the Color Changing Indicator (CCI), when the CCI comes in contact with the liquid food item. In an embodiment, the step of 302 further involves capturing an image of the biosensor on which the CCI is present, for example the bio-sensor 102 (FIG. 1) configured on a packaged container (for example, the container 100) containing a food item, and then the color of the CCI is determined by processing the captured image using appropriate image processing technique(s). As described previously, the color of the CCI is indicative of quality of the food item. The food item is made of a plurality of chemical components, and a plurality of physio-thermal properties of each of the one or more chemical components vary with degradation of the liquid food item. For each unique combination of the physio-thermal properties, the color of the CCI is different. This way the color of the CCI gives an indication of the quality of the food item. Along with the color of the CCI, the system 200 also collects information on ambient temperature and the relative humidity at which the container 100 is kept at. The information on the color of the CCI, and the ambient temperature and the relative humidity are then processed at step 304.

Figure 4:
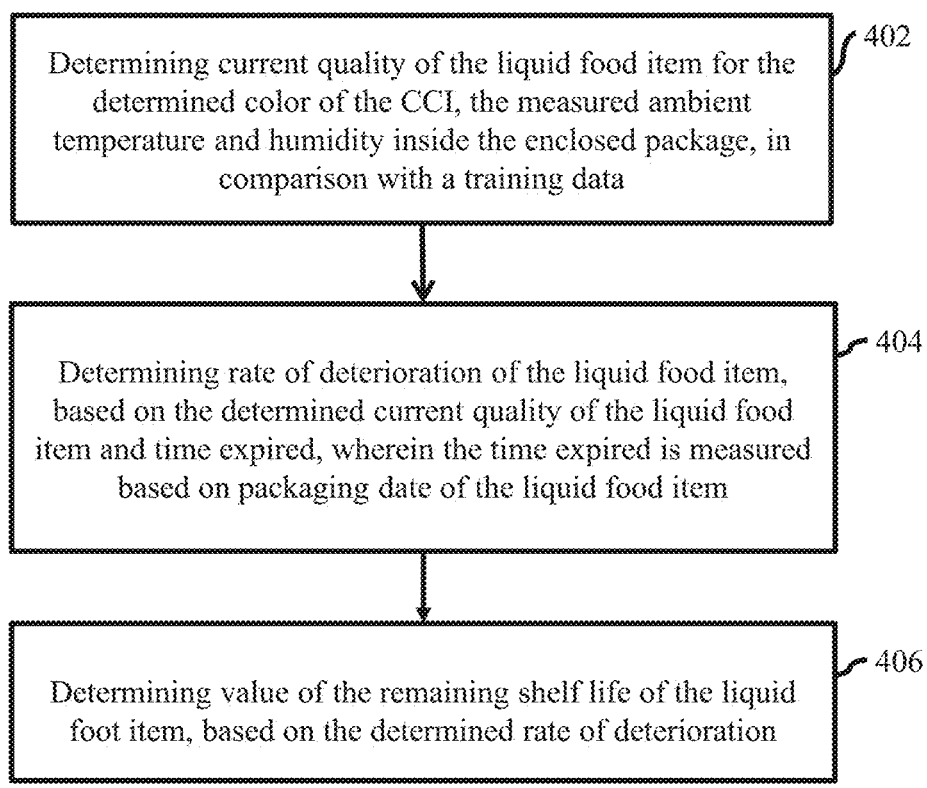
FIG. 4 is a flow diagram illustrating a method for determining remaining shelf life of a liquid food item stored in the liquid food container of FIG. 1, using the system of FIG. 2, in accordance with some embodiments of the present disclosure.

At 304, the method 300 includes predicting the quality of the food item based at least on the color of the biosensor by a pretrained machine learning data model. In an embodiment, the system 100 determines the quality of the food material in terms of a determined rate of deterioration of the food material. Various steps involved in the process of determining the quality of the food material are depicted in FIG. 4, method 400. The machine learning data model is trained on data which comprises information on quality of the food item corresponding to various combinations of the color of the CCI, and the ambient temperature and the relative humidity. Upon receiving the information on the determined color of the CCI, and the ambient temperature and the relative humidity (collectively referred to as 'real-time data'), for the food material for which the quality is to be determined, the machine learning data model identifies the quality of the food material by comparing the real-time data with the data in the machine learning data model. When a match is found for the real-time data in the machine learning data model (i.e. in the training data), corresponding quality is determined as the current quality of the food material, at step 402 of method 400.

Further, at step 404, the machine learning data model determines a rate of deterioration of the liquid food item, based on the determined current quality and time expired from date of packaging of the food material. In an embodiment, the date of packaging is identified automatically by the system 100, during processing of the image collected at step 302. In another embodiment, the date of packaging is manually fed to the system 100 as an input. The current quality determined at step 402 may be tagged with a percentage value (i.e. the food material is 60% good, 80% good and so on). Based on what percentage has deteriorated (for example, by 30%), and based on time taken for the food material quality to deteriorate to that extent (determined based on the date of packaging of the food material), the system 100 determines at step 404, a rate of deterioration of the liquid food material. Further, based on the determined rate of deterioration, the system 100 determines remaining shelf life of the food material, at step 406. For example, if the determined rate of deterioration indicates that the quality of the food material deteriorates at a rate of 10 percent per day, and 3 days have passed since date of packaging, the system 100 determines that the food material may be used/consumed safely for next 6 more days (i.e. remaining shelf life is 6, assuming that the food material is safe for consumption till the current quality hits 0%, however, appropriate value may be configured with the system 100).

Further, at step 306, the system 100 generates a result indicating the determined remaining shelf life of the food material, in a pre-configured format. In various embodiments, the steps in method 300 may be performed in the same order as depicted in FIG. 3, or in any alternate order that is technically feasible. In another embodiment, one or more steps in method 300 may be omitted.

Example Use-Case and Experimental Results:

The design of a colorimetric indicator targeting spoilage reaction(s) i.e. the biosensor which can be incorporated into the packaging itself, was used to test quality of orange juice which is packaged in a container. For the sensor to produce color, the biomarker must react with the sensor. For this purpose, the sensor must satisfy some criteria. E.g. Consider the below reaction, in general:

$$B+X \rightarrow Y \quad (1)$$

where X is some compound in the sensor which is specific to a biomarker B, and Y is the product formed. Here, the production of Y must produce some color, which could be proportional to its concentration. As the intensity of the color increases, the observer can infer that the biomarker is getting depleted.

Such an assay must be sensitive to changes in the biomarker concentration in the orange juice. Hence, it must be operational in the range of concentration that the biomarker goes through in the package.

Since X and Y are part of the sensor housed inside the package, they must be non-toxic The spoilage of orange juice occurs through both enzymatic and non-enzymatic pathways. In case of aseptically packaged orange juices, the enzymatic pathways are inhibited in order to prolong shelf life. Hence only the non-enzymatic browning occurs in such juices, during transportation & storage.

Figure 5A:
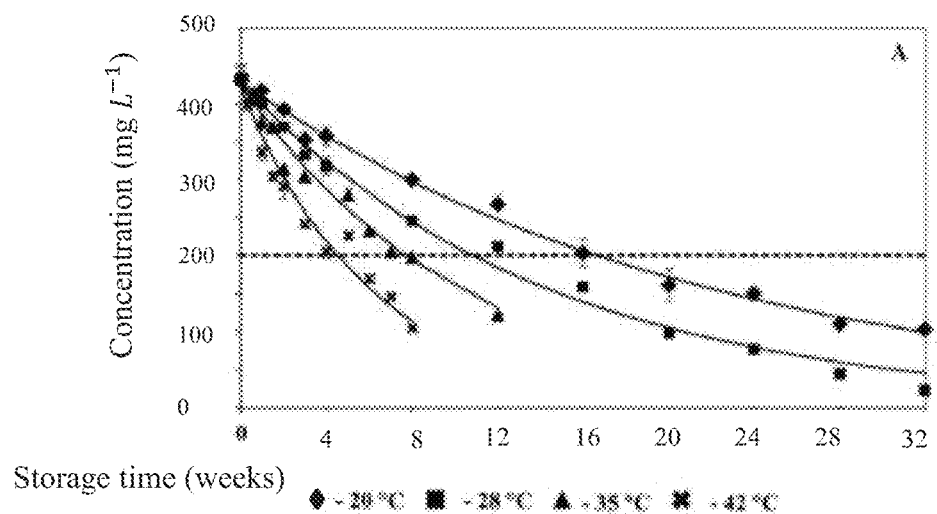
FIGS. 5A through 5E are example values of different parameters, obtained during an experimental conducted to predict quality of a liquid food item, using the system of FIG. 1, in accordance with some embodiments of the present disclosure.

The concentrations of compounds such as ascorbic acid, sugars (fructose, glucose, sucrose), dissolved & headspace oxygen, 5-hydroxymethyl furfural and furfural in orange juice changes (increases/decreases) over time at various temperatures. Degradation of ascorbic acid in orange juice over time is depicted in FIG. 5A. Orange juice is a rich source of Vitamin C (ascorbic acid), having ~400 mg/L at the time of packaging. The ascorbic acid degradation is one of the principal ways by which the quality of the orange juice is commonly judged. As can be seen in FIG. 5A, the concentration profile drops at every temperature. The dotted horizontal line at 200 mg/L indicates the threshold concentration, below which the juice is considered unacceptable for consumption. With increasing storage temperature, the ascorbic acid concentration reaches its threshold more rapidly.

Figure 5B:
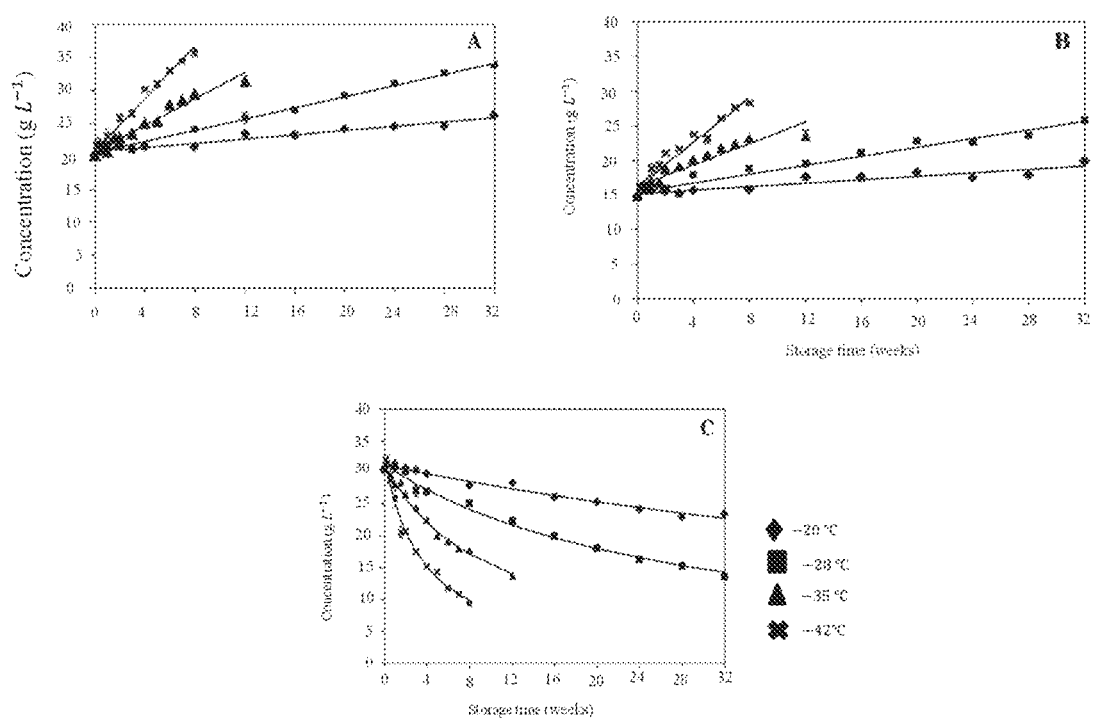

Similarly, FIG. 5B depicts change in concentration of fructose (A), glucose (B), and sucrose (C) in the orange juice over time. Orange juice contains sugars in the form of sucrose, glucose and fructose. Their concentration profiles vs storage time at different temperatures is shown FIG. 5B. As can be seen that the fructose and glucose concentrations continue to increase at all storage temperatures, whereas the sucrose profile drops as a result of acid catalyzed hydrolysis. The enzyme glucose oxidase has been known to specifically oxidize glucose into gluconic acid and hydrogen peroxide $$\text{Glucose} + \text{glucose oxidase} + O_2 \rightarrow \text{gluconic acid} + H_2O_2$$

$$H_2O_2 + \text{peroxidase} + O_2 \text{ acceptor (colorless)} \rightarrow H_2O + \text{Oxidised acceptor (colored)}$$

Figure 5C:
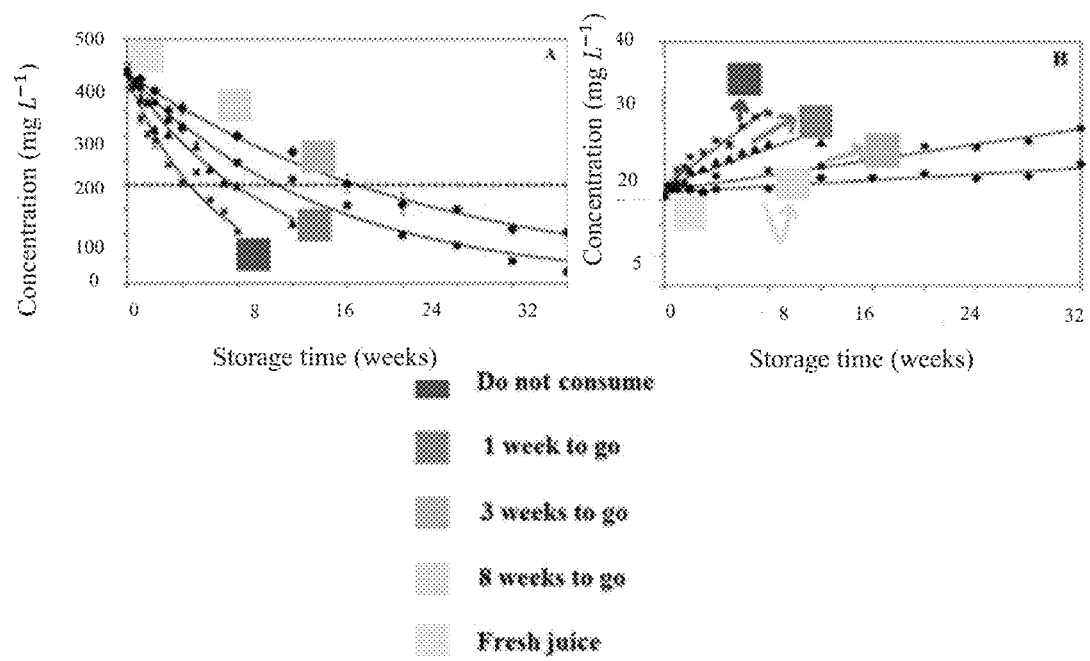

The formation of hydrogen peroxide was exploited by an enzyme peroxidase, which could produce color that was proportional to the glucose concentration. The enzymes in this assay were non-toxic too. This could serve as a potential sensing system for monitoring glucose concentration. Since the ascorbic acid concentration can be linked with the glucose concentration, one can get an estimate of the equivalent glucose concentration when the ascorbic acid reaches its threshold limit. As a result, one could semi-quantitively determine the ascorbic acid concentration, by observing the color shown by the glucose sensor. This is depicted in FIG. 5C.

Case study: A colorimetric sensor for glucose, which changes its color from yellow to dark green in the range over which the glucose concentration varies. The color of the sensor could correspond to some ascorbic acid concentration, which could be some point on an isotherm (T1). The time it would take for that isotherm to cross the threshold level could be the useful fresh life of the product, assuming the storage temperature is known to the consumer. If the storage temperature were to increase (>T1), the color would intensify, thereby corresponding to a different isotherm with a different shelf life. If the storage temperature were to be reduced (<T1), the color would not intensify any further beyond the predicted shelf life date, thereby notifying the consumer that the product has not yet reached its use by date. For finer differentiation of shelf life, a system could be developed whereby the consumer could capture the color of the sensor using a smartphone application. The application could have the glucose and ascorbic acid kinetic data stored inside, based on which it could inform the expected shelf, being able to finely differentiate between any two colors.

Figure 5D:
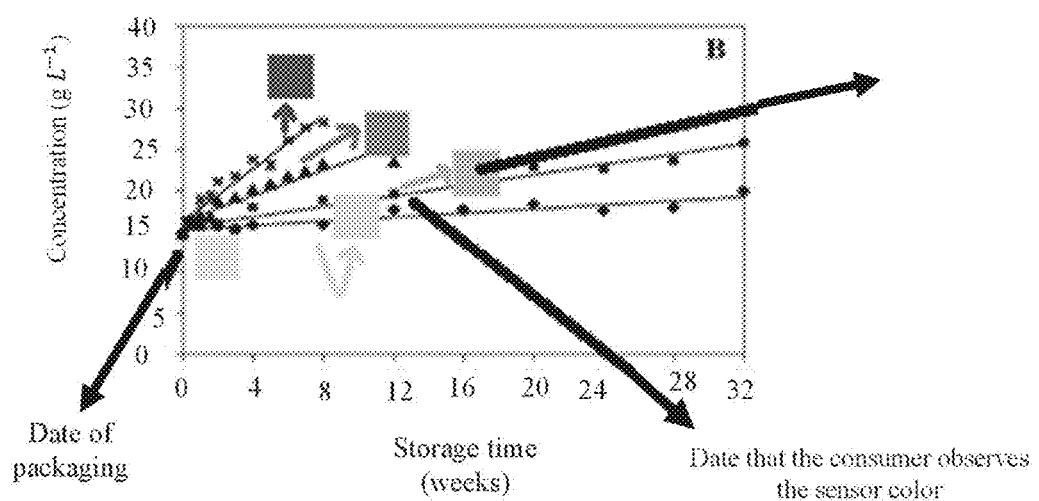

Even if the temperature history of the package was unknown to the consumer, there could be a way around this situation. For e.g. the date of packaging (mentioned on the package) and the date of observing the sensor reading would be known to the consumer. The consumer could feed these dates in a smartphone application containing the glucose kinetics database, along with the color shown by the sensor. Based on the time taken (date of observation–date of packaging=time elapsed) to reach to the observed color, the application could estimate the isotherm that the juice package would be following. Based on that isotherm, the application would be able to predict the remaining shelf life (if any) and inform the consumer about it. FIG. 5D illustrates this.

Furfural and 5-HMF

Figure 5E:
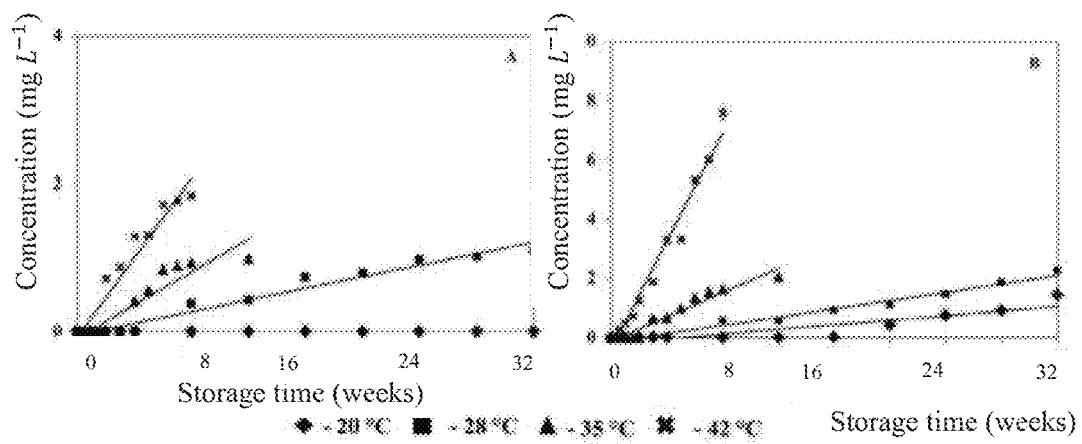

HMF (5-Hydroxymethylfurfural) and Furfural are the main products of ascorbic acid and sugar degradation. As can be seen in FIG. 5E, both furfural and HMF are "increasing" biomarkers. So, an assay prepared, would produce an intensifying color with storage. A colorimetric assay in this regard used was 2-thiobarbituric acid for HMF.

As seen from the previous section, it has been decided to target glucose as a biomarker for spoilage which will be correlated to the ascorbic acid (AA) threshold for considering the degradation in quality and labeling the data in terms of quality/freshness index w.r.t. to the AA threshold of 200 mg/L. The glucose conc. Change in the range of glucose 15 g/L (fresh juice) to 30 g/L (spoiled juice) is correlated to the AA change 400 mg/L (fresh juice) to 200 mg/L (spoiled juice) and there will considerable change in colour of the sensor strip as the glucose concentration changes from 15 g/L to 30 g/L i.e. The colour change in the glucose strip corresponds to the concentration of glucose in the juice and therefore indirectly is correlated to the corresponding AA conc in the juice at a given time. Several experiments were performed at various environmental conditions (at varying temperatures, humidity etc.) and the time-series data are labeled for quality change. A model was trained on these time-series data namely, environmental parameters like temp, humidity, concentration of glucose, concentration of AA, corresponding colour change for estimation in current time and prediction of quality for future instances in terms of remaining shelf life.

In real-time this data model may act as a soft sensor. The glucose sensor strip is embedded in the tetrapack and the strip changes colour when a certain concentration of glucose is reached. In an example implementation, a dedicated mobile application is developed which allows user to scan this colour change and enter the temperature conditions. The model/soft sensor in the background which is linked to this application (locally or over cloud) considers these parameters as input to the model, calculates the corresponding glucose concentration and AA concentration at that time. The model finally predicts the remaining shelf life based on these features and date of packaging and the same is shown to the user in the mobile application.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A method for non-invasive real-time prediction of quality of a liquid food item within enclosed package, comprising:
    capturing, via one or more hardware processors, an image of a Color Changing Indicator (CCI) in a bio-sensor strip forming a component of the enclosed package, when the liquid food item comes in contact with the CCI, wherein the CCI comprises:
        a transparent poly-di-methyl-siloxane (PDMS) substrate;
        a thin film layer of bio-edible and bio-compatible color changing pigments, wherein the bio-edible and bio-compatible color changing pigments change color by interacting with one or more chemical components of the liquid food item, wherein a plurality of physio-thermal properties of each of the one or more chemical components vary with degradation of the liquid food item; and
        an optical device, wherein the color change of the color changing pigments is visible through a transparent lens of the optical device;
    determining, via the one or more hardware processors, a color of the CCI;
    processing, via the one or more hardware processors using a machine learning data model, information on a) the determined color of the CCI, b) a measured ambient temperature inside the enclosed package while determining the color of the CCI and c) a measured relative humidity inside the enclosed package while determining the color of the CCI;
    determining, via the one or more hardware processors, a value of a remaining shelf life of the liquid food item by:
        determining a current quality of the liquid food item for the determined color of the CCI, the measured ambient temperature inside the enclosed package, and the measured relative humidity inside the enclosed package, in comparison with training data, wherein the training data used for training the machine learning data model comprises information on quality of the liquid food item corresponding to a plurality of combinations of a) a color of CCI, b) a value of the measured ambient temperature, and c) a value of the measured relative humidity;
        determining a rate of deterioration of the liquid food item, based on the determined current quality of the liquid food item, and time expired, wherein the time expired is measured based on packaging date of the liquid food item; and
        determining the value of the remaining shelf life of the liquid food item, based on the determined rate of deterioration; and
    generating, via the one or more hardware processors, a result indicating the determined value of the remaining shelf life of the liquid food item.

2. A system for non-invasive real-time prediction of quality of a liquid food item within enclosed package, comprising:
    one or more hardware processors;
    a communication interface; and
    a memory storing a plurality of instructions, wherein the plurality of instructions when executed, cause the one or more hardware processors to:
    capture an image of a Color Changing Indicator (CCI) in a bio-sensor strip forming a component of the enclosed package, when the liquid food item comes in contact with the CCI, wherein the CCI comprises:
        a transparent poly-di-methyl-siloxane (PDMS) substrate;
        a thin film of bio-edible and bio-compatible color changing pigments, wherein the bio-edible and bio-compatible color changing pigments change color by interacting with one or more chemical components of the liquid food item, wherein a plurality of physio-thermal properties of each of the one or more chemical components vary with degradation of the liquid food item; and
        an optical device, wherein the color change of the color changing pigments is visible through a transparent lens of the optical device;

process, using a machine learning data model, information on a) the determined color of the CCI, b) a measured ambient temperature inside the enclosed package while determining the color of the CCI, and c) a measured relative humidity inside the enclosed package while determining the color of the CCI;

determine a value of a remaining shelf life of the liquid food item by:

determining a current quality of the liquid food item for the determined color of the CCI, the measured ambient temperature inside the enclosed package, and the measured relative humidity inside the enclosed package, in comparison with training data, wherein the training data used for training the machine learning data model comprises information on quality of the liquid food item corresponding to a plurality of combinations of a) a color of CCI, b) a value of the measured ambient temperature, and c) a value of the measured relative humidity;

determining a rate of deterioration of the liquid food item, based on the determined current quality of the liquid food item, and time expired, wherein the time expired is measured based on packaging date of the liquid food item; and determining the value of the remaining shelf life of the liquid food item, based on the determined rate of deterioration; and generate a result indicating the determined value of the remaining shelf life of the liquid food item.

3. A non-transitory computer readable medium for non-invasive real-time prediction of quality of a liquid food item within enclosed package, wherein the non-transitory computer readable medium comprising a plurality of instructions, which when executed, cause:

capturing an image determining color of a Color Changing Indicator (CCI) in a bio-sensor strip forming a component of the enclosed package, when the liquid food item comes in contact with the CCI, via one or more hardware processors, wherein the CCI comprises:

a transparent poly-di-methyl-siloxane (PDMS) substrate;

a thin film layer of bio-edible and bio-compatible color changing pigments, wherein the bio-edible and bio-compatible color changing pigments change color by interacting with one or more chemical components of the liquid food item, wherein a plurality of physiothermal properties of each of the one or more chemical components vary with degradation of the liquid food item; and an optical device, wherein the color change of the color changing pigments is visible through a transparent lens of the optical device;

processing, using a machine learning data model, information on a) the determined color of the CCI, b) a measured ambient temperature inside the enclosed package while determining the color of the CCI, and c) a measured relative humidity inside the enclosed package while determining the color of the CCI;

determining a value of a remaining shelf life of the liquid food item by:

determining a current quality of the liquid food item for the determined color of the CCI, the measured ambient temperature inside the enclosed package, and the measured relative humidity inside the enclosed package, in comparison with training data, wherein the training data used for training the machine learning data model comprises information on quality of the liquid food item corresponding to a plurality of combinations of a) a color of CCI, b) a value of the measured ambient temperature, and c) a value of the measured relative humidity;

determining a rate of deterioration of the liquid food item, based on the determined current quality of the liquid food item, and time expired, wherein the time expired is measured based on packaging date of the liquid food item; and determining the value of the remaining shelf life of the liquid food item, based on the determined rate of deterioration; and generating a result indicating the determined value of the remaining shelf life of the liquid food item.

* * * * *